US012670993B2

(12) United States Patent
Hautala et al.

(10) Patent No.: US 12,670,993 B2
(45) Date of Patent: Jun. 30, 2026

(54) GENERATIVE AI TO CREATE TIME SERIES PREDICTION RADIOTHERAPY TREATMENT PLANNING SYSTEMS

(71) Applicant: SIEMENS HEALTHINEERS INTERNATIONAL AG, Steinhausen (CH)

(72) Inventors: Ismo Hautala, Espoo (FI); Esa Kuusela, Espoo (FI); Jarkko Peltola, Tuusula (FI); Lauri Halko, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 0 days.

(21) Appl. No.: 18/979,382

(22) Filed: Dec. 12, 2024

(65) Prior Publication Data

US 2026/0171242 A1    Jun. 18, 2026

(51) Int. Cl.
 *G16H 50/20* (2018.01)
 *G16H 40/60* (2018.01)

(52) U.S. Cl.
 CPC ............. *G16H 50/20* (2018.01); *G16H 40/60* (2018.01)

(58) Field of Classification Search
 CPC ............................... G16H 50/20; G16H 40/60
 See application file for complete search history.

(56) References Cited

U.S. PATENT DOCUMENTS

| | | | | |
|---|---|---|---|---|
| 6,356,437 B1* | 3/2002 | Mitchell | ................. | G06F 1/163 361/730 |
| 6,574,672 B1* | 6/2003 | Mitchell | ................. | G06F 1/163 709/200 |
| 6,592,641 B2* | 7/2003 | Alvin | ................. | B01D 46/0047 55/341.6 |
| 6,697,894 B1* | 2/2004 | Mitchell | ................. | G06F 1/163 361/679.55 |
| 6,863,868 B1* | 3/2005 | Alvin | ................. | B01D 39/2068 422/177 |
| 6,985,579 B2* | 1/2006 | Abood | ................. | H04M 1/0216 379/433.04 |
| 7,266,775 B2* | 9/2007 | Patitucci | ............... | G06F 16/252 715/735 |
| 7,308,550 B2* | 12/2007 | Cornett | ................ | G05B 19/056 711/170 |

(Continued)

OTHER PUBLICATIONS

Breunig, Int J Radiation Oncol Biol Phys, 2012, pp. e703-708.*

(Continued)

*Primary Examiner* — Michael I Ezewoko
(74) *Attorney, Agent, or Firm* — Foley & Lardner LLP

(57) ABSTRACT

A server monitors a sequence of screen captures from a radiotherapy treatment planning platform's user interface, operated by medical professionals. The server generates a training dataset comprising a time series of the screen captures and trains a machine learning model using this dataset. The trained model is configured to predict visual attributes of the user interface, determining the next screen's attributes based on prior interactions. When executed, the model predicts future visual attributes of the interface as a user interacts with the current screen, offering real-time guidance for navigating the treatment planning platform.

14 Claims, 3 Drawing Sheets

Monitor a sequence of screen captures generated from a user interface of a radiotherapy treatment planning platform operated by a set of medical professionals. 202

Generate a training dataset comprising a time series dataset corresponding to the sequence of screen captures. 204

Train a machine learning model, such that the machine learning model is configured to predict a visual attribute of a next screen capture of the user interface of the radiotherapy treatment planning platform based on at least one previous screen capture of the radiotherapy treatment planning platform. 206

Execute the machine learning model to predict a future visual attribute of a future screen capture of the radiotherapy treatment planning platform for the current screen capture of radiotherapy treatment planning platform being interacted with by a user. 208

(56) References Cited

U.S. PATENT DOCUMENTS

| 7,310,720 B2* | 12/2007 | Cornett | G05B 19/056 |
| | | | 711/170 |
| 7,329,344 B2* | 2/2008 | Jordan | C02F 3/1268 |
| | | | 210/310 |
| 7,344,643 B2* | 3/2008 | Elefritz, Jr. | C02F 3/1221 |
| | | | 210/607 |
| 7,387,723 B2* | 6/2008 | Jordan | C02F 3/1268 |
| | | | 210/500.21 |
| 7,390,399 B2* | 6/2008 | Dennis, II | C02F 1/008 |
| | | | 210/205 |
| 7,464,339 B2* | 12/2008 | Keenan, Jr. | H04L 67/34 |
| | | | 715/762 |
| 7,473,364 B2* | 1/2009 | Abu-Orf | C02F 11/02 |
| | | | 210/625 |
| 7,512,593 B2* | 3/2009 | Karklins | G05B 19/05 |
| | | | 711/111 |
| 7,569,147 B2* | 8/2009 | Curtis | C02F 3/12 |
| | | | 210/625 |
| 7,718,065 B2* | 5/2010 | Jordan | C02F 3/1221 |
| | | | 210/197 |
| 7,844,904 B2* | 11/2010 | Patitucci | G06F 16/252 |
| | | | 715/746 |
| 7,860,874 B2* | 12/2010 | Karklins | G05B 19/05 |
| | | | 700/83 |
| 7,867,401 B2* | 1/2011 | Dennis, II | C02F 1/008 |
| | | | 700/266 |
| 7,876,098 B2* | 1/2011 | Zhu | G01R 33/34046 |
| | | | 324/318 |
| 8,473,852 B2* | 6/2013 | Russell | G05B 15/02 |
| | | | 715/757 |
| 8,548,231 B2* | 10/2013 | Shet | G06V 40/103 |
| | | | 706/56 |
| 8,548,567 B2* | 10/2013 | Maschke | A61B 6/481 |
| | | | 600/467 |
| 8,623,213 B2* | 1/2014 | Liu | C02F 3/1221 |
| | | | 210/259 |
| 8,732,850 B2* | 5/2014 | Gudenus | G06F 21/10 |
| | | | 726/27 |
| 8,751,616 B2* | 6/2014 | Karklins | G05B 19/4185 |
| | | | 700/83 |
| 8,801,931 B2* | 8/2014 | Liu | C02F 3/1215 |
| | | | 210/603 |
| 8,850,346 B2* | 9/2014 | Keenan, Jr. | H04N 1/00976 |
| | | | 715/771 |
| 8,854,202 B2* | 10/2014 | Anderson, Jr. | G06F 3/048 |
| | | | 340/501 |
| 8,894,855 B2* | 11/2014 | Liu | C02F 3/121 |
| | | | 210/603 |
| 8,933,930 B2* | 1/2015 | Han | G06T 11/206 |
| | | | 700/17 |
| 9,019,858 B2* | 4/2015 | Harris | H04L 47/83 |
| | | | 455/67.11 |
| 9,087,309 B2* | 7/2015 | Faragoi, Jr. | G05B 15/02 |
| 9,170,702 B2* | 10/2015 | Hersche | G05B 23/027 |
| 9,251,480 B2* | 2/2016 | Faragoi, Jr. | G05B 15/02 |
| 9,274,684 B2* | 3/2016 | Han | G05B 15/02 |
| 9,423,789 B2* | 8/2016 | Cornett | G05B 19/4185 |
| 9,519,393 B2* | 12/2016 | Grossele | G05B 15/02 |
| 9,542,059 B2* | 1/2017 | Han | G05B 23/027 |
| 9,619,125 B2* | 4/2017 | Ruszala | G08B 25/008 |
| 9,690,265 B2* | 6/2017 | Casilli | G05B 13/048 |
| 9,721,459 B2* | 8/2017 | El-Mankabady | G08B 3/10 |
| 9,741,002 B2* | 8/2017 | Faragoi, Jr. | G06Q 30/0641 |
| 9,746,844 B2* | 8/2017 | Bryant | G06F 16/27 |
| 9,871,777 B2* | 1/2018 | Swaminathan | H04W 12/06 |
| 9,872,376 B2* | 1/2018 | Burton | H05H 9/00 |
| 9,908,712 B2* | 3/2018 | Edwards | B65G 35/06 |
| 9,929,872 B2* | 3/2018 | Keenan, Jr. | G06F 3/0484 |
| 10,007,240 B2* | 6/2018 | Landou | G08B 19/00 |
| 10,019,129 B2* | 7/2018 | Han | G06Q 30/00 |
| 10,084,611 B2* | 9/2018 | Hersche | H04L 12/2814 |
| 10,289,079 B2* | 5/2019 | Ambühl | G05B 15/02 |
| 10,339,097 B2* | 7/2019 | El-Mankabady | G08B 21/02 |
| 10,360,312 B2* | 7/2019 | Mattson | G06T 19/00 |
| 10,376,217 B2* | 8/2019 | Schmidt | A61B 5/055 |
| 10,561,443 B2* | 2/2020 | Gilson | A61B 90/37 |
| 10,600,514 B2* | 3/2020 | Haas | G06T 7/149 |
| 10,618,536 B2* | 4/2020 | El Fassi | B61L 3/127 |
| 10,964,092 B2* | 3/2021 | Engel | A61B 6/466 |
| 11,077,923 B2* | 8/2021 | Kriews | B63G 8/08 |
| 11,101,032 B2* | 8/2021 | Kohle | G06V 10/454 |
| 11,406,844 B2* | 8/2022 | Yang | A61B 6/5217 |
| 11,478,210 B2* | 10/2022 | Rosselet | A61B 6/5229 |
| 11,478,660 B2* | 10/2022 | Nord | G06T 7/11 |
| 11,786,204 B2* | 10/2023 | Rosselet | A61B 6/5229 |
| | | | 600/1 |
| 11,798,755 B2* | 10/2023 | Janakiraman | H01H 9/167 |
| 11,868,452 B2* | 1/2024 | Kröselberg | H04L 67/12 |
| 12,011,616 B2* | 6/2024 | Kapatoes | A61N 5/1075 |
| 2003/0051456 A1* | 3/2003 | Alvin | B01D 46/58 |
| | | | 55/486 |
| 2004/0260431 A1* | 12/2004 | Keenan, Jr. | G06F 3/0484 |
| | | | 700/297 |
| 2006/0126893 A1* | 6/2006 | Tran | G06T 7/254 |
| | | | 382/101 |
| 2007/0051677 A1* | 3/2007 | Curtis | C02F 3/1221 |
| | | | 210/625 |
| 2009/0313495 A1* | 12/2009 | Krishnan | G16H 10/60 |
| | | | 726/4 |
| 2010/0278420 A1* | 11/2010 | Shet | G06F 18/24765 |
| | | | 382/156 |
| 2011/0029897 A1* | 2/2011 | Russell | G05B 15/02 |
| | | | 715/757 |
| 2011/0137667 A1* | 6/2011 | Faragoi, Jr. | G05B 15/02 |
| | | | 705/1.1 |
| 2011/0137668 A1* | 6/2011 | Faragoi, Jr. | G06Q 10/06 |
| | | | 705/1.1 |
| 2012/0108965 A1* | 5/2012 | Lazebnik | A61B 8/4254 |
| | | | 600/459 |
| 2012/0201421 A1* | 8/2012 | Hartmann | A61B 6/5235 |
| | | | 382/103 |
| 2012/0290539 A1* | 11/2012 | Bryant | G06F 16/113 |
| | | | 707/661 |
| 2013/0046421 A1* | 2/2013 | El Fassi | B61L 23/041 |
| | | | 701/2 |
| 2013/0082832 A1* | 4/2013 | Anderson, Jr. | G05B 23/027 |
| | | | 340/501 |
| 2013/0083012 A1* | 4/2013 | Han | G06T 11/206 |
| | | | 345/419 |
| 2013/0083035 A1* | 4/2013 | Han | G06T 11/206 |
| | | | 345/473 |
| 2013/0086152 A1* | 4/2013 | Hersche | G05B 23/0216 |
| | | | 709/203 |
| 2013/0086497 A1* | 4/2013 | Ambuhl | G05B 15/02 |
| | | | 715/762 |
| 2013/0086521 A1* | 4/2013 | Grossele | G05B 15/02 |
| | | | 715/810 |
| 2013/0142310 A1* | 6/2013 | Fahimian | A61N 5/103 |
| | | | 378/65 |
| 2014/0018940 A1* | 1/2014 | Casilli | G05B 15/02 |
| | | | 700/29 |
| 2014/0241174 A1* | 8/2014 | Harris | H04L 47/83 |
| | | | 370/252 |
| 2014/0244823 A1* | 8/2014 | Cornett | G05B 19/4185 |
| | | | 709/223 |
| 2014/0258940 A1* | 9/2014 | Han | G06F 3/0484 |
| | | | 715/854 |
| 2014/0359752 A1* | 12/2014 | Swaminathan | G06Q 10/06 |
| | | | 726/16 |
| 2014/0379138 A1* | 12/2014 | Keenan, Jr. | G06F 3/0484 |
| | | | 700/275 |
| 2015/0278932 A1* | 10/2015 | Faragoi, Jr. | G06Q 30/0641 |
| | | | 705/27.1 |
| 2016/0041537 A1* | 2/2016 | Landou | G08B 19/00 |
| | | | 700/275 |
| 2016/0104085 A1* | 4/2016 | Faragoi, Jr. | G06Q 10/06 |
| | | | 705/7.23 |
| 2016/0148498 A1* | 5/2016 | Ruszala | G08B 25/003 |
| | | | 340/506 |

(56) References Cited

U.S. PATENT DOCUMENTS

| | | | |
|---|---|---|---|
| 2017/0046012 A1* | 2/2017 | Han | G08B 13/19682 |
| 2017/0076585 A1* | 3/2017 | El-Mankabady | G08B 27/006 |
| 2017/0086758 A1* | 3/2017 | Mc Carthy | A61B 6/4085 |
| 2017/0090680 A1* | 3/2017 | Hersche | H04L 12/282 |
| 2017/0091200 A1* | 3/2017 | El-Mankabady | G08B 21/02 |
| 2017/0340354 A1* | 11/2017 | Gilson | A61B 90/37 |
| 2017/0340901 A1* | 11/2017 | Haas | G06T 7/149 |
| 2018/0000435 A1* | 1/2018 | Liu | A61B 6/5235 |
| 2018/0043183 A1* | 2/2018 | Sheng | A61N 5/103 |
| 2019/0030371 A1* | 1/2019 | Han | A61N 5/1039 |
| 2019/0147457 A1* | 5/2019 | Magowan | G06Q 30/018 |
| | | | 705/317 |
| 2020/0058390 A1* | 2/2020 | Kohle | G16H 30/40 |
| 2020/0265353 A1* | 8/2020 | Srivastava | G06F 30/23 |
| 2021/0097156 A1* | 4/2021 | Kröselberg | G06F 21/31 |
| 2021/0299470 A1* | 9/2021 | Nord | G06T 7/0012 |
| 2021/0299471 A1* | 9/2021 | Yang | A61B 6/502 |
| 2022/0099585 A1* | 3/2022 | Denneler | C23C 28/02 |
| 2023/0012859 A1* | 1/2023 | Janakiraman | G08C 17/02 |
| 2023/0100510 A1* | 3/2023 | Hoelzer | G16H 10/60 |
| | | | 345/629 |
| 2023/0343121 A1* | 10/2023 | Ullaskrishnan | G16H 30/40 |
| 2024/0005048 A1* | 1/2024 | Hofford | G06F 30/12 |
| 2024/0096089 A1* | 3/2024 | Regensburger | G06V 10/993 |
| 2024/0331148 A1* | 10/2024 | Roser | G09G 5/377 |
| 2024/0374227 A1* | 11/2024 | Regensburger | G06T 11/006 |
| 2024/0378773 A1* | 11/2024 | Regensburger | A61B 6/5247 |
| 2025/0073494 A1 | 3/2025 | Kuusela et al. | |
| 2025/0149165 A1 | 5/2025 | Kuusela et al. | |
| 2025/0185983 A1* | 6/2025 | Groten | A61B 5/4561 |
| 2025/0200331 A1 | 6/2025 | Kuusela et al. | |
| 2025/0349399 A1* | 11/2025 | Crabtree | G16H 50/50 |

OTHER PUBLICATIONS

Jaffray, Elsevier, 2002, pp. 1337-1349.*
Kalet, PubMed, 1997, pp. 327-339.*
Liu, ArXiv, Mar. 2024, pp. 1-12.*
Moreira, Elsevier, Apr. 2024, pp. 1-6.*
Retif, Elsevier, Mar. 2024, pp. 1-10.*
Rietzel, Elsevier, 2005, pp. 1535-1550.*
Schreibmann, Elsevier, 2008, pp. 578-586.*
Shin, Elsevier, 2020, pp. 1-10.*
Stieb, HHS, 2020, pp. 1-16.*
Van Sörnsen De Koste, Elsevier, 2005, pp. 334-339.*
Zhang, ArXiv, 2021, pp. 1-23.*

* cited by examiner

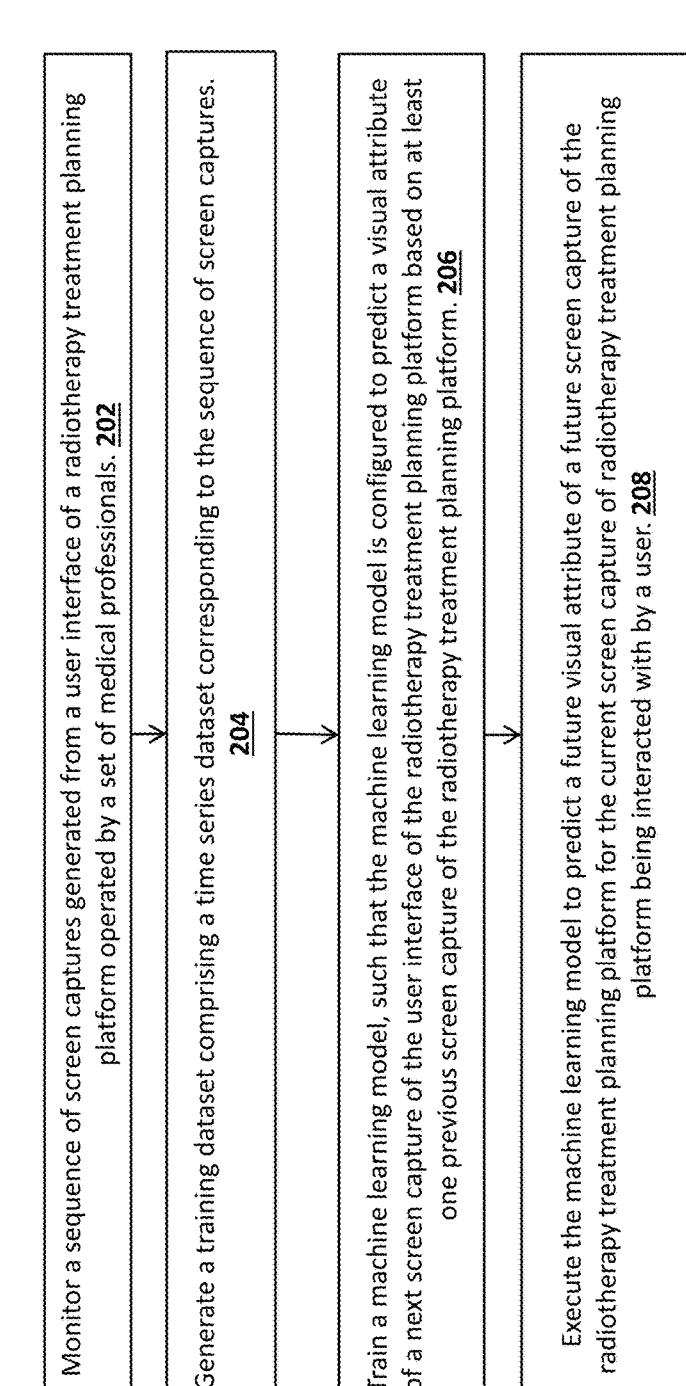

200

Monitor a sequence of screen captures generated from a user interface of a radiotherapy treatment planning platform operated by a set of medical professionals. 202

Generate a training dataset comprising a time series dataset corresponding to the sequence of screen captures. 204

Train a machine learning model, such that the machine learning model is configured to predict a visual attribute of a next screen capture of the user interface of the radiotherapy treatment planning platform based on at least one previous screen capture of the radiotherapy treatment planning platform. 206

Execute the machine learning model to predict a future visual attribute of a future screen capture of the radiotherapy treatment planning platform for the current screen capture of radiotherapy treatment planning platform being interacted with by a user. 208

FIG. 2

GENERATIVE AI TO CREATE TIME SERIES PREDICTION RADIOTHERAPY TREATMENT PLANNING SYSTEMS

TECHNICAL FIELD

This application relates generally to training generative AI models for radiotherapy treatment planning systems.

BACKGROUND

Radiotherapy or radiation therapy (RT) is one of the main modalities used in cancer treatment, and RT treatment planning (RTTP) is a complex process that contains specific guidelines, protocols, and instructions adopted by different medical professionals, such as clinicians, medical device manufacturers, and the like. Medical professionals strive to deliver the safest and most effective treatment to patients.

The RTTP creation typically involves a collaboration of multiple professionals and an automated computer model (e.g., treatment planner or plan optimizer). The initial treatment plan is usually created based on the best available information at the time, tailored from standard treatment protocols to suit the individual patient. Specifically, various attributes are inputted by a medical professional into a treatment planning software (TPS), which is an interface or a platform of the treatment planner, where the computer model optimizes the RTTP using those attributes.

The TPS usually consists of platform having a highly complex series of interactive interfaces, each containing multiple menus, buttons, and data fields that medical professionals must navigate to perform tasks and ultimately input the medical characteristics of the RTTP. The sheer volume of options and the non-linear workflows make it challenging for users to know which steps to take next, especially when each clinic may have its own preferred methods. This complexity often results in a steep learning curve, requiring extensive training and experience to navigate the system efficiently and correctly. Navigating the TPS generally requires specialized knowledge, necessitating thorough training for new clinic personnel before they can effectively use the TPS. This training is important when staff start using a new planning system or when the software is updated to support new optimization or treatment techniques, ensuring alignment with current clinical practices. Achieving full expertise takes even longer, and the rapidly evolving RT domain requires continuous learning of new aspects of treatment planning. Educating new or junior staff members adds to the workload of senior personnel, which is highly undesirable.

SUMMARY

Training medical professionals to be proficient with complex treatment planning systems (TPS) typically requires a significant amount of time due to the vast number of features and the multiple ways users can achieve desired outcomes. Traditional user manuals are insufficient for covering all the potential workflows and variations in how the TPS is used. Recently, Large Language Models (LLMs) have gained attention as potential solutions to streamline the user interface and enhance training for TPS users. Commonly proposed uses for LLMs include providing a natural language question-and-answer interface for "help" functionality or enabling direct TPS control through natural language commands.

However, conventional LLMs suffer from technical problems. For instance, while LLMs may soon offer a reliable method for organizing help features, they are not tailored to adapt to the various ways in which different clinics use the TPS. Standard LLMs may not account for the diverse practices and workflows unique to each clinic, and collecting the specific training data needed for further LLM customization can be challenging. Moreover, incorporating LLM-driven guidance into the existing TPS structure-rich with visual elements like menus, buttons, fields, and graphs-presents integration difficulties, as the LLM's natural language processing capabilities do not easily translate to such a visual interface.

The methods and systems discussed herein are (at least partially) directed toward training and using a generative AI model to predict how the visual interface of a TPS will change as a user progresses through tasks. The model disclosed herein can monitor the TPS screen in real-time (or near real-time) and can predict the next visual state based on the user's actions. Unlike other conventional approaches, the model discussed herein can monitor the visual elements and can guide the user in accordance with the sequences of screens navigated by the user. Moreover, the prediction provided by the model may be visual in nature. For instance, the model may be trained and configured to predict the next graphical user interface that should ultimately lead to the desired outcome. Accordingly, the model discussed herein improves the functionality of other machine learning models configured to perform the same tasks. For instance, by not including actual treatment data, the model discussed herein can be trained using less data and can be executed using less computing power and in a faster manner (because it uses less, sometimes not substantive data). Unlike many other existing solutions, the model discussed herein does compute cost function for a potential or candidate RTTP. Therefore, the model discussed herein can run more efficiently using less computing power and provide an answer in less time.

The prediction provided by the model discussed herein may allow the model to suggest actions, making the workflow more intuitive and efficient for users. The model disclosed herein may be trained on time-series screen captures of previous medical professionals working with the TPS. Additional training can be done using video recordings from clinical settings or algorithmically generated inputs, enabling the model to predict the next screen in a sequence. In one example of the implementation, a Video Stream Model (VSM) takes a series of screen captures and predicts the next frame based purely on the visual data. It should be noted that the model differs from other models or AI copilots because the model discussed here is trained based on the visual aspects of the TPS and not necessarily interaction data generated as a result of the interaction of the medical professional and the TPS. For instance, the model discussed herein may not necessarily review the validity of the RTTP or be trained to optimize one or more treatment attributes. Instead, the model may be trained using the visual elements of how previous users have used a particular TPS. These unique characteristics allow the model discussed herein to run more efficiently (e.g., faster) and require less training data.

In some aspects, the techniques described herein relate to a method including: monitoring, by at least one processor, a sequence of screen captures generated from a user interface of a radiotherapy treatment planning platform operated by a set of medical professionals; generating, by the at least one processor, a training dataset including a time series dataset corresponding to the sequence of screen captures; training, by the at least one processor, a machine learning model using the training dataset, such that the machine learning model is configured to predict a visual attribute of a next screen capture of the user interface of the radiotherapy treatment planning platform based on a previous screen capture of the radiotherapy treatment planning platform; and executing, by the at least one processor, the machine learning model to predict a future visual attribute of a future screen capture of the radiotherapy treatment planning platform for a current screen capture of the radiotherapy treatment planning platform being interacted with by a user.

In some aspects, the techniques described herein relate to a method, further including: displaying, by the at least one processor, a warning notification when a future screen capture deviates from the future visual attribute predicted by the machine learning model.

In some aspects, the techniques described herein relate to a method, wherein the machine learning model is further trained using a video recording a medical professional interacting with the radiotherapy treatment planning platform.

In some aspects, the techniques described herein relate to a method, further including: redacting, by the at least one processor, at least one visual attribute within at least one screen capture within the training dataset.

In some aspects, the techniques described herein relate to a method, wherein the machine learning model is further trained using an auditory instruction by a medical professional interacting with the radiotherapy treatment planning platform.

In some aspects, the techniques described herein relate to a method, further including: displaying, by the at least one processor, the at least one future visual attribute.

In some aspects, the techniques described herein relate to a method, wherein the machine learning model is trained for a particular clinic.

In some aspects, the techniques described herein relate to a computer readable medium including a set of non-transitory instructions that when executed cause a processor to: monitor a sequence of screen captures generated from a user interface of a radiotherapy treatment planning platform operated by a set of medical professionals; generate a training dataset including a time series dataset corresponding to the sequence of screen captures; train a machine learning model using the training dataset, such that the machine learning model is configured to predict a visual attribute of a next screen capture of the user interface of the radiotherapy treatment planning platform based on a previous screen capture of the radiotherapy treatment planning platform; and execute the machine learning model to predict a future visual attribute of a future screen capture of the radiotherapy treatment planning platform for a current screen capture of the radiotherapy treatment planning platform being interacted with by a user.

In some aspects, the techniques described herein relate to a computer readable medium, wherein the set of instructions further cause the processor to: display a warning notification when a future screen capture deviates from the future visual attribute predicted by the machine learning model.

In some aspects, the techniques described herein relate to a computer readable medium, wherein the machine learning model is further trained using a video recording a medical professional interacting with the radiotherapy treatment planning platform.

In some aspects, the techniques described herein relate to a computer readable medium, wherein the set of instructions further cause the processor to: redact at least one visual attribute within at least one screen capture within the training dataset.

In some aspects, the techniques described herein relate to a computer readable medium, wherein the machine learning model is further trained using an auditory instruction by a medical professional interacting with the radiotherapy treatment planning platform.

In some aspects, the techniques described herein relate to a computer readable medium, wherein the set of instructions further cause the processor to: display the at least one future visual attribute.

In some aspects, the techniques described herein relate to a computer readable medium, wherein the machine learning model is trained for a particular clinic.

In some aspects, the techniques described herein relate to a system including a server configured to: monitor a sequence of screen captures generated from a user interface of a radiotherapy treatment planning platform operated by a set of medical professionals; generate a training dataset including a time series dataset corresponding to the sequence of screen captures; train a machine learning model using the training dataset, such that the machine learning model is configured to predict a visual attribute of a next screen capture of the user interface of the radiotherapy treatment planning platform based on a previous screen capture of the radiotherapy treatment planning platform; and execute the machine learning model to predict a future visual attribute of a future screen capture of the radiotherapy treatment planning platform for a current screen capture of the radiotherapy treatment planning platform being interacted with by a user.

In some aspects, the techniques described herein relate to a system, wherein the server is further configured to: display a warning notification when a future screen capture deviates from the future visual attribute predicted by the machine learning model.

In some aspects, the techniques described herein relate to a system, wherein the machine learning model is further trained using a video recording a medical professional interacting with the radiotherapy treatment planning platform.

In some aspects, the techniques described herein relate to a system, wherein the server is further configured to: redact at least one visual attribute within at least one screen capture within the training dataset.

In some aspects, the techniques described herein relate to a system, wherein the machine learning model is further trained using an auditory instruction by a medical professional interacting with the radiotherapy treatment planning platform.

In some aspects, the techniques described herein relate to a system, the server is further configured to: display the at least one future visual attribute.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 2 shows an operational workflow of a method performed in hardware and software computing components that host and execute an AI-enabled treatment planning system in accordance with an embodiment.

DETAILED DESCRIPTION

Figure 1:
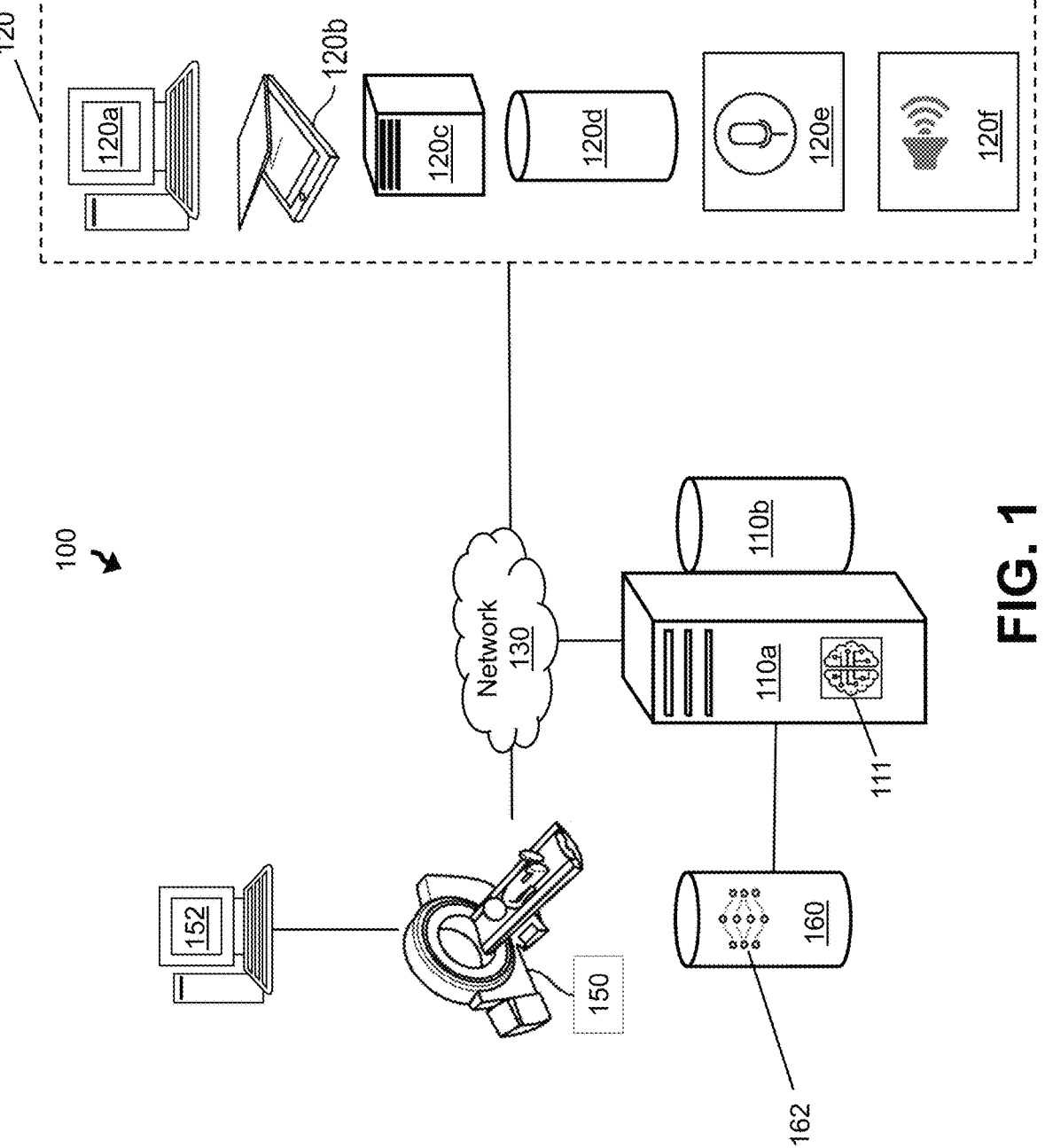
FIG. 1 illustrates components of a system implementing an AI-enabled treatment planning system in accordance with an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used, and/or other changes may be made without departing from the spirit or scope of the present disclosure. The illustrative embodiments described in the detailed description are not meant to limit the subject matter presented.

FIG. 1 illustrates components of a system 100 for an AI-enabled treatment planning system, according to an embodiment. The system 100 may include an analytics server 110*a*, a system database 110*b*, a machine learning model 111, end-user devices 120*a*-120*f* (collectively end-user devices 120), a medical device 150, a medical device computer 152, a database 160, and a radiotherapy plan optimizer 162. Various components depicted in FIG. 1 may belong to a radiation therapy treatment clinic at which patients may receive radiation therapy treatment, in some cases via one or more radiation therapy machines (e.g., the medical device 150).

The system 100 is not confined to the components described herein and may include additional or other components, not shown for brevity, which are to be considered within the scope of the embodiments described herein.

The above-mentioned components may be connected to each other through one or more networks 130. Examples of the network 130 may include, but are not limited to, private or public local-area networks (LAN), wireless local-area networks (WLAN), metropolitan-area networks (MAN), wide-area networks (WAN), and the Internet. The network 130 may include wired and/or wireless communications according to one or more standards and/or via one or more transport mediums. The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), or EDGE (Enhanced Data for Global Evolution) network.

The analytics server 110*a* may generate and display an electronic platform (also referred to herein as the treatment planning system or TPS) configured to interface a user with the radiotherapy plan optimizer 162 and/or (indirectly with) the machine learning model 111 and for receiving patient information (via various sources) and visualization preferences/instructions. The analytics server 110*a* may then output the results of the execution of the machine learning model 111 and the radiotherapy plan optimizer 162 using the TPS. In some embodiments, the TPS and/or the interaction interface of the platform may be populated via the radiotherapy plan optimizer 162 itself.

The TPS may include graphical user interfaces (GUIs) displayed on each of the end-user devices 120, the medical device 150, and/or the medical device computer 152. An example of the TPS generated and hosted by the analytics server 110*a* may be a web-based application or a website configured to be displayed on different electronic devices, such as mobile devices, tablets, personal computers, and the like.

The TPS hosted on the analytics server 110*a* or another device of the system 100 includes collaboration software accessible to the user devices 120 of the participating members, such that multiple medical professionals can collaborate and view the visualizations provided by the analytics server 110*a*. The collaboration software may include any type of software facilitating user-group collaborations, which may include live interaction software (e.g., teleconferencing software) or asynchronous collaborations (e.g., online postings).

The collaboration software may also facilitate communication between one or more medical professionals and the analytics server 110*a* and/or the radiotherapy plan optimizer 162. For instance, the platform provided or hosted by the analytics server 110*a* may include an input element (e.g., visual, textual, or auditory), allowing users (e.g., one or more medical professionals) to input their desired treatment plan attributes. The TPS may also display predicted outputs by the radiotherapy plan optimizer 162. As described herein, the analytics server 110*a* may also display outputs predicted by the machine learning model 111.

The information displayed by the analytics server 110*a* of the TPS can include any contextual data associated with a user's input while generating a treatment plan. For example, the analytics server may display any data needed to generate a treatment plan for one or more patients. Non-limiting examples may include data associated with a patient to be treated (e.g., plan objectives) or visualization attributes (e.g., what the medical professional desires to view), missing data, incorrect data, contextual data associated with how to operate the radiotherapy plan optimizer 162, and the like.

The analytics server 110*a* may be any computing device comprising a processor and non-transitory machine-readable storage capable of executing the various tasks and processes described herein. The analytics server 110*a* may employ various processors, such as central processing units (CPU) and graphics processing units (GPU), among others. Non-limiting examples of such computing devices may include workstation computers, laptop computers, server computers, and the like. While the system 100 includes a single analytics server 110*a*, the analytics server 110*a* may include any number of computing devices operating in a distributed computing environment, such as a cloud environment.

End-user devices 120 may be any computing device comprising a processor and a non-transitory machine-readable storage medium capable of performing the various tasks and processes described herein. Non-limiting examples of an end-user device 120 may be a workstation computer, laptop computer, tablet computer, or server computer. In operation, various users may use end-user devices 120 to access the GUI operationally managed by the analytics server 110*a*. Specifically, the end-user devices 120 may include a clinic computer 120*a*, a clinic server 120*b*, and medical professional devices 120*c*, which may include any electronic devices operated by members of the Tumor Board, medical professionals, and scientists that access and review various types of patient-related treatment data and RTTPs for the patient, among other types of data and information exchanges.

In a non-limiting example, multiple medical professionals may operate the medical professional devices 120*c* to review patient-related treatment data to develop a consensus on a treatment for the patient. Even though referred to herein as "end-user" devices, these devices may not always be operated by end-users. For instance, the clinic server 120*b* may not be directly used by an end-user. However, the results stored on the clinic server 120*b* may be used to populate various GUIs accessed by an end-user via the medical professional device 120*c*. Patient-related information generated by the various types of devices in system 100, outside the context of the AI treatment planning agent, may be stored within database 100*b*. The stored patient data may be referenced by the analytics server 110*a* for training the machine learning model 111.

The medical device 150 may be a radiation therapy machine configured to implement a patient's radiotherapy treatment. The medical device 150 may also be in communication with a medical device computer 152 that is configured to display various GUIs discussed herein. For instance, the analytics server 110*a* may display the results predicted by the radiotherapy plan optimizer 162 onto the computing devices described herein.

The machine learning model 111 may be stored in the system database 110*b*. The machine learning model 111 may be configured or trained to automatically generate text, image, or video responses based on inputs received at a user interface or other types of inputs (e.g., speech captured at a conference room microphone or microphone of an end-user device 120).

In some embodiments, the analytics server 110*a* may retrieve data inputted via the TPS and execute the radiotherapy plan optimizer 162 to generate one or more treatment attributes for an RTTP complying with any radiation therapy plan objectives based on patient attributes of a patient for which the radiotherapy treatment plan is being generated. The radiotherapy plan optimizer 162 can be stored in the database 160. The radiotherapy plan optimizer 162 can generate the one or more treatment attributes, for example, by iteratively calculating the one or more treatment attributes where, with each iteration, the radiotherapy plan optimizer 162 can revise the one or more treatment attributes of the RTTP in accordance with a cost value.

The analytics server 110*a* may deploy the radiotherapy plan optimizer 162 to generate an RTTP for a patient based on patient attributes and one or more treatment attributes received from one or more end-user devices 120 (via the TPS). The radiotherapy plan optimizer 162 may iteratively calculate one or more treatment attributes of the RTTP. For instance, with each iteration, the radiotherapy plan optimizer 162 may generate a candidate RTTP having various attributes. The plan optimizer 162 may then use one or more loss functions to calculate a cost value for the generated candidate RTTP. The cost value may indicate a likelihood of the candidate RTTP violating a set of rules, whether internal and/or external rules. For instance, the cost value may indicate whether the candidate RTTP violates any of the plan objectives. The radiotherapy plan optimizer 162 may analyze the cost value. If needed (e.g., when the cost value satisfies a threshold), the radiotherapy plan optimizer 162 may revise the candidate RTTP and re-execute its loss function to generate a new cost value.

Depending on whether the new cost function is increasing or decreasing, the plan optimizer computer model may revise the candidate RTTP again and recalculate the cost value. The radiotherapy plan optimizer 162 may continue this iterative approach until converging upon an RTTP (or the final RTTP) that has a cost value that satisfies a threshold. In some implementations, the treatment attribute for the patient may also indicate how the radiotherapy treatment may be combined or sequentially implemented with other types of treatment modalities (e.g., surgery, chemotherapy).

In some embodiments, the analytics server 110*a* or the end-user device 120 can use the RTTP to automatically control the medical device 150 based on attributes of the RTTP to treat the patient. The system database 110*b* may contain data used to train the machine learning model 111 to help with users operating the TPS.

FIG. 2 shows an operational workflow of method 200 performed in hardware and software computing components within an AI-enabled treatment planning system in accordance with an embodiment. The method 200 may include steps 202-208. However, other embodiments may include additional or alternative steps or may omit one or more steps altogether. The method 200 is described as being executed by a server, such as the analytics server described in FIG. 1. However, one or more steps of the method 200 may be executed by any number of computing devices operating in the distributed computing system described in FIG. 1. For instance, one or more computing devices may locally perform some or all of the steps described in FIG. 2.

At step 202, the analytics server may monitor a sequence of screen captures generated from a user interface of a radiotherapy treatment planning platform operated by a set of medical professionals.

As discussed herein, the screen captures may refer to a time series of screen captures or a collection of one or more images taken from the TPS interface as it is being used by a user (e.g., a physicist, a clinician, or otherwise a medical professional). Moreover, as used herein, the radiotherapy treatment planning platform refers to the interfaces of the TPS. The screen captures can be recorded at regular intervals or triggered when a significant change in the interface occurs, such as a user selecting a menu option or adjusting a treatment parameter. Another trigger for capturing a screen could be a change in the system's state, such as when a new tool is activated, or a dialogue box opens. As discussed herein, this data can be ingested by a machine learning model to predict the next screen (e.g., a visual element of the next screen), reflecting the likely state of the interface after the next major user interaction or system change, helping guide users through the workflow.

Each screen capture may include a timestamp that can be used to generate a time-series dataset corresponding to progression indicating how the TPS was used to generate a RTTP.

In some embodiments, the analytics server may monitor a sequence of screen captures generated from the user interface of a radiotherapy treatment planning platform (e.g., TPS) as it is being operated by a group of medical professionals. In those embodiments, the server captures and tracks visual changes within the interface in real-time or near-real-time, allowing it to observe the actions taken by users during their workflow. This sequence of screen captures can provide the analytics server with a detailed view of the user's interactions with the TPS.

In some embodiments, the analytics server may monitor the interactions of users with the TPS by performing a periodic screen capture (e.g., generating images associated with the TPS) of the user's computer. Using the captured images, the analytics server may generate a sequence of screen captures that reflect the visual changes occurring in the user interface of the TPS as medical professionals perform their tasks and navigate through different interfaces to generate the RTTP. These screen captures may be taken in real-time or near-real time, recording each action a user takes, such as selecting menu options, entering data into fields, or adjusting treatment parameters. In some embodiments, the analytics server may record (e.g., generate a video file) the interface of the TPS.

By continuously monitoring these visual interactions, the analytics server can track the workflow progression, understand user behavior, and later use this data for predictive analysis or training purposes. Additionally, the analytics server may capture the sequence of interfaces. For instance, the monitored data may show a particular pattern of the users and how they may use a common pattern in how to navigate the TPS.

At step 204, the analytics server may generate a training dataset comprising a time series dataset corresponding to the sequence of screen captures.

Using the monitored data, the analytics server may generate a training dataset. The training dataset for the system may be generated by collecting video recordings or aggregating the captured images of medical professionals using TPS during their normal workflows. These recordings capture the sequence of screen changes and interactions made by the users as they navigate through various tasks in the TPS. The captured data may also indicate a clickstream and interaction data (e.g., where and when users clicked on). Additionally, spoken annotations provided by the professionals during or after the recordings can be included to add contextual information about the planning process.

The analytics server may aggregate the monitored/captured data into a training dataset. In some embodiments, the analytics server may perform one or more pre-processing protocols. For instance, in some embodiments, the analytics server may generate a time-stamped time series of the captured data. In another embodiment, the analytics server may redact sensitive data from the screen captures or the contextual data that is used to augment the training dataset.

The training dataset may capture a comprehensive view of how medical professionals interact with the TPS during their routine workflows. The training dataset may include a series of screen captures or video recordings that document every action taken by the users while navigating the TPS and generating the RTTP. These screen captures may reflect the dynamic changes in the user interface as the professionals engage with various features, such as selecting options from menus, entering data into fields, and making adjustments to treatment parameters. The visual representation of these interactions may be directly used for training the model to understand how the TPS is used in different clinical settings and/or in different clinics.

Additionally, the server can incorporate contextual information in order to augment the training dataset, such as patient data or user instructions, to enhance the understanding of these interactions. As used herein, contextual information may refer to any additional data beyond the screen captures that can enhance the model's predictions. This information may include a list of tokens representing patient-specific data retrieved from a database, such as medical history or treatment goals. It can also encompass natural language inputs, either spoken or written by the clinician or derived from the screen captures and processed by a specialized Large Language Model (LLM). This contextual data can provide the machine learning model (to be trained) with a deeper understanding of the clinical scenario, enabling it to offer more accurate predictions and tailored guidance within the TPS.

In some embodiments, the analytics server may use a secondary model to generate or transform the contextual data. For instance, the analytics server may use a visual embedding model. As used herein, the visual embedding model may refer to any specialized neural network designed to convert screen captures from the TPS into serialized data, such as natural language descriptions or latent vector representations. This conversion may allow the machine learning model to extract meaningful semantic and structural information from the raw bitmap images within the screen captures. For example, the visual embedding model can analyze a screen capture to identify and describe user interface elements like menus, data fields, or open dialogues. It can also extract numeric or textual data displayed on the screen, transforming it into a structured format that can be processed by another model, such as an LLM.

The visual embedding model may be trained using annotated screen captures. Accordingly, the visual embedding model can learn to recognize and interpret the specific elements and data displayed within the TPS interface. The training may be tailored to a specific TPS, ensuring that the model understands the unique layout and functionalities of that TPS. In some embodiments, the model is designed to be generalizable across different clinics using the same TPS, meaning it does not require further retraining or adjustment to account for variations in workflow between clinics.

In some embodiments, the training dataset can be generated by recording video sessions of clinicians performing various tasks within the TPS for a particular clinic. These recordings can be further enhanced with spoken annotations provided by the clinicians either during the session or afterward, allowing one or more users to offer additional context about their actions. This process enables a clinic to gather a clinic-specific training dataset that captures how the TPS is utilized in their particular environment. As a result, the machine learning model may be trained, such that it is configured for a particular clinic and uses clinic-specific rules and protocols to make its predictions.

Once this clinic-specific dataset is collected, the machine learning model can be trained by building on an existing, pre-trained generic model. This approach allows the model to be further fine-tuned with data that reflects the unique workflows and practices of the clinic. By continuing the training process using this localized data, the model can become better suited to predict user actions and provide real-time guidance tailored to the specific ways the TPS is used in that clinic, improving both accuracy and relevance in day-to-day operations.

The analytics server can augment the training dataset with several additional types of information to enhance the model's predictive capabilities. For instance, in addition to the screen captures, the training dataset can be enhanced via spoken or written annotations provided by the users during or after their interactions. These annotations may offer contextual information, explaining why specific actions were taken or clarifying the reasoning behind certain choices. For example, a user might explain why they adjusted a treatment parameter in response to a particular patient condition. In another example, the user may describe why a particular path was taken and why the order of the inputs was provided the way they were provided. This information can help the machine learning model understand not just what actions are being performed but the intent behind those actions, making it more effective at predicting future user behavior.

In some embodiments, the analytics server may augment the training dataset using patient data, such as the type of cancer being treated, the treatment goals, any specific instructions provided by the attending physician, or patient attributes (e.g., BMI, tumor location, and the like). By incorporating this additional layer of context, the model can better tailor its predictions to the specific needs of the clinic and the patients being treated.

In some embodiments, the analytics server may augment the training dataset using user interaction logs, which capture detailed records of actions such as mouse clicks, keystrokes, and menu selections. These logs, when aligned with the screen captures, can provide a more granular view of how users are interacting with the TPS, adding precision and depth to the dataset.

In some embodiments, the analytics server may augment the training dataset using external clinical guidelines and treatment protocols that guide medical decision-making in radiation therapy. By embedding these guidelines, the model can align its predictions with best practices and regulatory standards, supporting clinicians in making clinically sound choices. Finally, historical performance data from past planning sessions and treatment outcomes can be included in the dataset. This historical data may allow the model to recognize patterns that have led to successful treatment plans, helping it to provide guidance informed by real-world success stories. Together, these sources of data create a comprehensive and highly informative training dataset for the model.

Additionally, algorithmically generated video inputs can be used to further refine the model.

The contextual data discussed herein, combined with the screen captures and annotations, may form a rich, multi-dimensional training set that enables the system to learn both the visual patterns of interaction and the underlying medical reasoning that guides the use of the TPS.

At step 206, the analytics server may train a machine learning model using the training dataset, such that the machine learning model is configured to predict a visual attribute of a next screen capture of the user interface of the radiotherapy treatment planning platform based on at least one previous screen capture of the radiotherapy treatment planning platform.

Using the training dataset discussed herein, the analytics server may train the machine learning model. By ingesting and combining the visual data with interaction logs and patient information discussed herein, the model may learn to develop a more sophisticated understanding of the workflows involved in treatment planning. This multimodal approach may allow the model to provide tailored guidance, aligning its predictions not only with the visual flow of the interface but also with the unique needs of each case. The training may be any deep learning technique combined with any supervised, unsupervised, or semi-supervised technique. The model may be trained using the training data, such that the model can predict a visual attribute of a subsequent interface of a TPS give a current interface of the TPS and/or a sequence of past interfaces of the TPS. For instance, the model may be configured to ingest a graphical user interface of the TPS and predict how the next step should look (e.g., a set of visual attributes of the next GUI).

The machine learning model may be further refined using historical performance data and/or real-time TPS information. Using historical data during training can help the model identify patterns that lead to successful treatment plans, allowing it to learn from past successes and mistakes. Real-time TPS state data, such as the current phase of the treatment plan or active tools, can allow the model to track how the TPS evolves throughout the workflow. By incorporating all these elements, the machine learning model can become more robust and context-aware, enabling it to predict user actions with greater accuracy and offer real-time guidance that aligns with both the TPS's current state and the medical professional's clinical goals.

Effectively, the model may be configured to predict the next steps or actions a user is likely to take within the TPS based on their current interactions. For instance, the model may process real-time (or near-real-time) screen captures and user inputs to anticipate how the visual interface will evolve as the user navigates through the system. The model may also take into account contextual information, such as patient data, current system state, and user behavior patterns, allowing it to predict specific actions like selecting a menu option, adjusting treatment parameters, or opening a dialogue box. Additionally, the model may be trained to predict how the interface should change in response to these actions, providing a continuous, real-time understanding of the workflow. This predictive capability can help guide users through the complex TPS environment by offering suggestions for the next steps or highlighting potential options to optimize the treatment planning process.

In some embodiments, a Video Stream Model (VSM) can be trained using the training dataset. Specifically, a dataset comprised of screen captures from medical professionals interacting with TPS can be ingested by the VSM. In some embodiments, the training dataset may also be augmented using the data and methods discussed herein.

The training process may begin by collecting a series of screen captures that document the progression of user interactions with the TPS, capturing actions such as selecting menu options, entering treatment parameters, and adjusting settings. These sequences may be then paired with any available contextual information, such as patient data or task-related annotations, which provide additional insight into why certain actions are taken.

The VSM may be trained to predict the next screen (e.g., at least one visual attribute of the next screen) in the sequence by analyzing patterns in the previous screens. For example, given a set of frames showing a user setting treatment parameter, the VSM can learn to predict what the next screen will display based on the sequence of previous actions. For instance, the VSM may predict what the menu option for the subsequent screen would indicate. In some embodiments, the training may be performed in a supervised learning manner, where the actual next screen serves as the ground truth, and the model iteratively improves by reducing the difference between its predictions and the real screens.

To further refine the model, advanced techniques like Generative Adversarial Networks (GANs) may be used, where a generator predicts the next screen, and a discriminator evaluates how accurate that prediction is. Over time, the VSM may become proficient at forecasting future screens, providing real-time guidance to users by predicting what their next steps should be based on their interactions with the TPS.

At step 208, the analytics server may execute the machine learning model to predict a future visual attribute of a future screen capture of the radiotherapy treatment planning platform for a current screen capture of the radiotherapy treatment planning platform being interacted with by a user.

As discussed herein, the model may be configured to predict the next actions a user is likely to take (or should take) within the TPS based on their current interactions. The model may provide real-time (or near-real-time) guidance, suggesting the next steps in the workflow or highlighting potential options for the user based on the patterns it has learned during training.

The model may ingest real time (or near-real-time) data indicating how a user is navigating a TPS. As a result, the model may predict visual attributes of a subsequent screen. The analytics server may use a variety of methods to provide the predicted information to the user.

In some embodiments, the model may be configured to detect deviations from expected workflows. For example, if a user is about to take an action that differs from the predicted optimal path or could potentially lead to an error, the model can flag this behavior and provide corrective suggestions and/or send warnings to the user. This capability helps prevent mistakes and ensures that users follow best practices or clinic-specific protocols during treatment planning. In some embodiments, the model can also function as a proactive assistant, offering predictive visual aids or tooltips. For example, the model may display a predicted future screen or suggest a sequence of actions that would help the user complete their task more efficiently. This allows the system to act like a virtual expert, guiding users through complex workflows and improving their proficiency in using the TPS.

In some embodiments, the predictions generated by the machine learning model can be used to guide users by showing them what action is expected next based on their previous interactions with the TPS. For example, the analytics server may suggest which menu item to select, what value to input or adjust, or which dialog box to complete. These predicted screen images can be created in the background, and the analytics server may only display them to the user when it has a high level of confidence that the predicted action aligns with the user's current workflow.

Additionally, or alternatively, the analytics server can use predictions to alert the user when they are about to perform a potentially harmful or incorrect action. By flagging deviations from expected workflows, the model helps prevent errors that could compromise the RTTP. If the model is equipped with contextual information-such as patient data or task-specific details—the analytics server may generate predicted screens only when explicitly requested by the user, guiding them through specific situations that require additional assistance.

In the embodiments where a visual embedding model is used, the predictions can be enhanced by analyzing the content of the predicted screens to offer more detailed contextual guidance. For instance, the machine learning model may recognize that the user is performing a specific task, such as adjusting treatment parameters, and suggest the next action accordingly. The machine learning model may also support creating multiple consecutive predicted screens, allowing the system to guide users through more complex workflows that involve multiple steps or phases, providing a comprehensive, step-by-step visual roadmap for the task at hand.

In contrast to traditional methods of using paper or electronic manuals to provide generic guidance on how to navigate the software, the machine learning model trained and implemented using the methods and systems discussed herein can act as an experienced colleague, assisting the user step-by-step through the workflow. Using the methods and systems discussed herein, the analytics server may present the user with small, concrete actions that can be taken to move forward in the planning process in real-time or near-real-time. This approach allows the user to proceed efficiently through the workflow, with personalized, real-time guidance based on the specific clinical situation. As a result, the methods and systems discussed herein significantly reduce the time needed to navigate complex tasks, helping the user complete a thorough and approved radiotherapy plan more quickly and accurately than with traditional manual guidance or conventional LLMs.

In an example, a medical physicist uses a TPS to develop a radiotherapy plan for a cancer patient. The physicist begins by selecting the appropriate patient case and reviewing the tumor location. As they work through the steps of adjusting treatment beams and defining dose distributions, the system, powered by the generative AI model discussed herein, continuously monitors the user's actions by capturing screen images and analyzing the inputs.

As the physicist moves through the workflow (e.g., different GUIs of the TPS), the model predicts a visual attribute of the next GUI of the TPS based on past interactions, patient-specific data, and the current screen layout.

Based on the predicted visual attribute, the model can determine whether the physicist has navigated to the next GUI that matches the visual attributes of the predicted next GUI. If the visual attribute indicates that the physicist has navigated to a different page/GUI, the system may display an alert and guide the physicist to the right next step. For example, the system could display a small notification suggesting a particular menu option. Alternatively, the system might automatically prepare the next screen or dialog box, making it easier for the physicist to continue working without manually navigating through the interface.

If the physicist is about to make a mistake or has made a mistake, such as inputting a dose value in the wrong field, the model can detect this deviation from the expected workflow and provide an alert, suggesting the correct action. Additionally, if the user is unsure of what to do next, they can request guidance, and the system will visually display the next predicted step, much like a virtual assistant offering expert advice.

Figure 3:
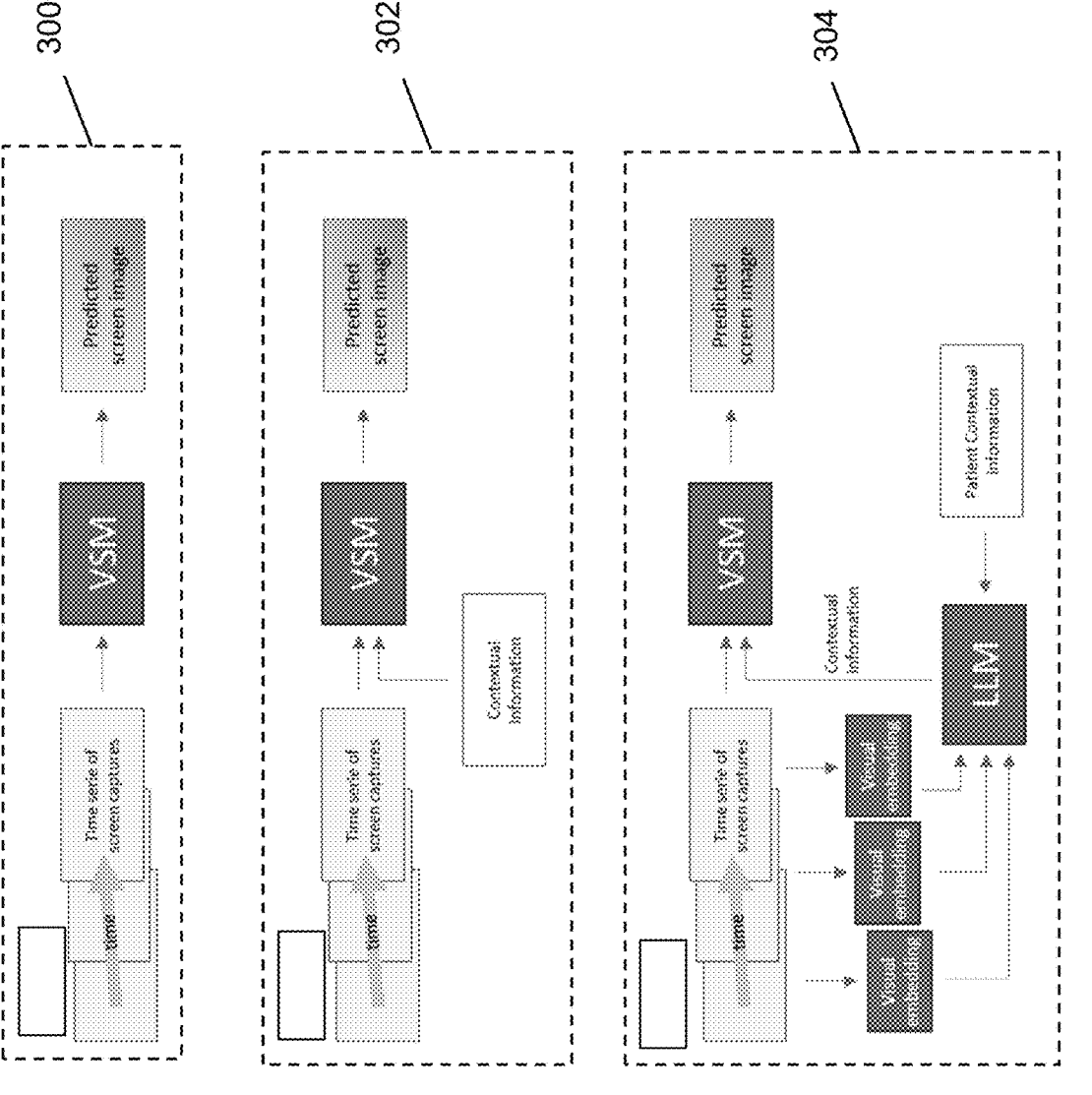
FIG. 3 illustrates a non-limiting example of a data flow within an AI-enabled treatment planning system in accordance with an embodiment.

Referring now to FIG. 3, non-limiting examples of data flow within an AI-enabled treatment planning system are depicted. In the depicted examples, a generative machine learning model is trained to predict how the user interface of a TPS will visually change over time as users perform various tasks. When trained, the model can be used to continuously monitor the TPS interface (e.g., as it is being used by a user), predicting upcoming screen changes based on user actions in real-time or near-real-time.

In the depicted embodiments, the model is a VSM. However, the methods and systems discussed herein apply to all machine learning models. Therefore, no limitation is intended.

An embodiment 300 depicts one non-limiting implementation of a VSM that involves using a series of variable-length screen captures as input, with the VSM trained to predict the next screen in the sequence. In this approach, the VSM operates solely on the visual data presented in these screen captures without requiring additional contextual information like patient data or TPS states. The VSM is tasked with learning the patterns of user interactions by observing how the interface evolves over time.

To evaluate the accuracy of the VSM's predictions, the system can calculate the pixel differences between the predicted screen and the actual next screen in the sequence. This method quantifies how closely the VSM's prediction aligns with the real screen, helping to fine-tune its accuracy. Additionally, to ensure compliance with privacy and data sensitivity requirements, the screen captures can be pre-processed to filter out (e.g., redact) irrelevant or sensitive information, such as patient names, identifiers, or temporary data that does not contribute to the training. This allows the VSM to focus solely on the relevant interface components, improving the efficiency of its predictions while maintaining the privacy of sensitive data. Moreover, this allows the VSM to not learn (and prevent accidental sharing of) confidential patient data.

In embodiment 302, the VSM ingests both screen captures and contextual information as input in order to enhance its predictive capabilities. Along with the visual data from the TPS interface, the VSM incorporates relevant patient information, such as medical history, treatment goals, prognosis information, and physician instructions. This added context allows the VSM to better understand the specific case and tailor its predictions to the clinical situation. By doing so, the VSM can predict not only the next screen but also suggest actions based on the patient's treatment plan and the current state of the system.

The VSM can also factor in the TPS's operational state when making predictions. For instance, the VSM may consider which features or menus are currently active, what tools the user has selected, and the progress made in the workflow. This enables the VSM to generate highly relevant predictions that go beyond the visual layout of the screen and align with the user's workflow and system status. If the user has reached a specific stage of treatment planning, the VSM can anticipate the next logical action or system change, streamlining the process and minimizing unnecessary/incorrect/inefficient steps.

Additionally, the VSM can incorporate spoken explanations or other real-time feedback from the user. For example, if the user verbally indicates they are about to adjust a treatment parameter, the VSM can integrate this information and predict the appropriate tool or screen. This multi-faceted approach provides dynamic, real-time (or near-real-time) guidance, not only predicting the next screen but also understanding the reasoning behind the user's actions. This results in more accurate, context-aware assistance, reducing errors and improving overall workflow efficiency within the TPS.

In the last embodiment, 304, the AI-enabled treatment planning system includes both a VSM and an LLM, linked together by a visual-embedding model. In this embodiment, the visual-embedding model converts the screen captures or images from the TPS into either natural language descriptions or latent-space vector representations. These representations may capture the essential information from the TPS interface, such as menus, data fields, or graphical elements, in a way that can be interpreted by the LLM.

Once the image data is converted into a corresponding visual embedding, the LLM may process the output of the visual-embedding model along with contextual information, such as patient-specific data or the current TPS state. The LLM, trained to understand both the clinical context and the structure of the TPS, can generate a natural language explanation or structured information that informs the next prediction. For example, the LLM might interpret a screen containing dose parameters and predict that the next action is likely to involve adjusting a treatment beam based on the current patient's case.

Finally, in the embodiment 304, the VSM leverages the enriched output from the LLM to predict the next screen in the TPS interface. By combining the visual data with natural language interpretations and clinical context, the VSM can provide more accurate and context-aware predictions of user actions. This integrated system not only predicts visual transitions but also generates meaningful insights into the user's workflow, helping guide users through complex tasks with personalized, step-by-step assistance that adapts to the clinical scenario and user behavior.

In a non-limiting example of the embodiment 304, a medical professional using a TPS to design a radiotherapy plan for a patient adjusts the dosage parameters on the screen. As they interact with the interface, the visual-embedding model converts the screen capture into a latent vector representation or natural language description, such as "current screen shows dose adjustment for a tumor in the left lung." This data is then transmitted to the LLM, which combines it with patient-specific information, like the tumor's location and prescribed treatment goals. The LLM interprets this context and generates a prediction for the next likely action, such as "adjust beam intensity" or "navigate to the next planning step." The VSM then predicts the next screen interface based on this combined input/prediction of the LLM. For example, the VSM may predict a screen showing the next step in the beam adjustment workflow, offering real-time guidance and suggestions to the user as they proceed through the treatment planning process.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means, including memory sharing, message passing, token passing, network transmission, etc.

The actual software code or specialized control hardware used to implement these systems and methods is not limited to the claimed features or this disclosure. Thus, the operation and behavior of the systems and methods were described without reference to the specific software code, and it is understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate the transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disc, and Blu-ray disc, where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
monitoring, by at least one processor, a sequence of screen captures generated from a user interface of a radiotherapy treatment planning platform operated by a set of medical professionals;
generating, by the at least one processor, a training dataset comprising a time series dataset corresponding to the sequence of screen captures and a visual difference between at least two screen captures based on a pixel difference between the at least two screen captures, wherein at least one visual attribute within at least one screen capture within the training dataset is redacted;
training, by the at least one processor, a machine learning model using the training dataset such that the machine learning model is configured to predict a visual attribute of a next screen capture of the user interface of the radiotherapy treatment planning platform based on a previous screen capture of the radiotherapy treatment planning platform;
executing, by the at least one processor, the machine learning model to predict a future visual attribute of a future screen capture of the radiotherapy treatment planning platform for a current screen capture of the radiotherapy treatment planning platform being interacted with by a user; and
displaying, by the at least one processor, a warning notification when the future screen capture deviates from the future visual attribute predicted by the machine learning model.

2. The method of claim 1, wherein the machine learning model is further trained using a video recording a medical professional interacting with the radiotherapy treatment planning platform.

3. The method of claim 1, wherein the machine learning model is further trained using an auditory instruction by a medical professional interacting with the radiotherapy treatment planning platform.

4. The method of claim 1, further comprising:
displaying, by the at least one processor, the at least one future visual attribute.

5. The method of claim 1, wherein the machine learning model is trained for a particular clinic.

6. A non-transitory computer readable medium comprising a set instructions that when executed cause a processor to:
monitor a sequence of screen captures generated from a user interface of a radiotherapy treatment planning platform operated by a set of medical professionals;
generate a training dataset comprising a time series dataset corresponding to the sequence of screen captures and a visual difference between at least two screen captures based on a pixel difference between the at least two screen captures, wherein at least one visual attribute within at least one screen capture within the training dataset is redacted;
train a machine learning model using the training dataset, such that the machine learning model is configured to predict a visual attribute of a next screen capture of the user interface of the radiotherapy treatment planning platform based on a previous screen capture of the radiotherapy treatment planning platform;
execute the machine learning model to predict a future visual attribute of a future screen capture of the radiotherapy treatment planning platform for a current screen capture of the radiotherapy treatment planning platform being interacted with by a user; and
display a warning notification when the future screen capture deviates from the future visual attribute predicted by the machine learning model.

7. The computer readable medium of claim 6, wherein the machine learning model is further trained using a video recording a medical professional interacting with the radiotherapy treatment planning platform.

8. The computer readable medium of claim 6, wherein the machine learning model is further trained using an auditory instruction by a medical professional interacting with the radiotherapy treatment planning platform.

9. The computer readable medium of claim 6, wherein the set of instructions further cause the processor to:
display the at least one future visual attribute.

10. The computer readable medium of claim 6, wherein the machine learning model is trained for a particular clinic.

11. A system comprising a server configured to:

monitor a sequence of screen captures generated from a user interface of a radiotherapy treatment planning platform operated by a set of medical professionals;

generate a training dataset comprising a time series dataset corresponding to the sequence of screen captures and a visual difference between at least two screen captures based on a pixel difference between the at least two screen captures, wherein at least one visual attribute within at least one screen capture within the training dataset is redacted;

train a machine learning model using the training dataset, such that the machine learning model is configured to predict a visual attribute of a next screen capture of the user interface of the radiotherapy treatment planning platform based on a previous screen capture of the radiotherapy treatment planning platform;

execute the machine learning model to predict a future visual attribute of a future screen capture of the radiotherapy treatment planning platform for a current screen capture of the radiotherapy treatment planning platform being interacted with by a user; and display a warning notification when the future screen capture deviates from the future visual attribute predicted by the machine learning model.

12. The system of claim 11, wherein the machine learning model is further trained using a video recording a medical professional interacting with the radiotherapy treatment planning platform.

13. The system of claim 11, wherein the machine learning model is further trained using an auditory instruction by a medical professional interacting with the radiotherapy treatment planning platform.

14. The system of claim 11, the server is further configured to:

display the at least one future visual attribute.

* * * * *